United States Patent [19]

Varma

[11] 4,091,036
[45] May 23, 1978

[54] 17-ALKYLTHIO (AND ARYLTHIO)-1',2',3',4'-TETRAHYDROANDROSTENO [16 α, 17 α-B]NAPHTHALENES AND DERIVATIVES

[75] Inventor: Ravi K. Varma, Belle Mead, N.J.

[73] Assignee: E. R. Squibb & Sons, Inc., Princeton, N.J.

[21] Appl. No.: 796,292

[22] Filed: May 12, 1977

[51] Int. Cl.² ............................................. C07J 1/00
[52] U.S. Cl. .................................. 260/397.45; 260/397.3
[58] Field of Search ...................................... 260/397.45

[56] References Cited
U.S. PATENT DOCUMENTS

| 3,937,720 | 2/1976 | Varmi et al. | 260/397.45 |
|---|---|---|---|
| 3,944,584 | 3/1976 | Chao et al. | 260/397.45 |
| 3,971,773 | 7/1976 | Cimarusti et al. | 260/239.55 R |
| 3,994,935 | 11/1976 | Varmi et al. | 260/397.45 |

Primary Examiner—Elbert L. Roberts
Attorney, Agent, or Firm—Lawrence S. Levinson; Merle J. Smith; Donald J. Barrack

[57] ABSTRACT

Steroids having the formula

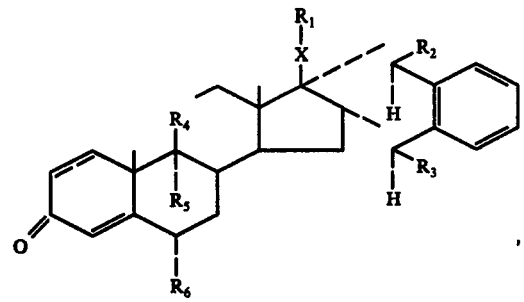

wherein X is

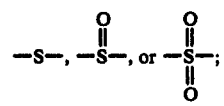

$R_1$ is alkyl, aryl or acyloxyalkyl; $R_2$ and $R_3$ are the same or different and are hydrogen, alkyl, alkoxy, carboalkoxy, formyl,

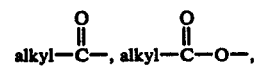

hydroxy, halogen, phenyl or cyano, with the proviso that when $R_2$ and $R_3$ are different, one of $R_2$ and $R_3$ is hydrogen; $R_4$ is carbonyl, β-hydroxymethylene or β-acyloxymethylene; $R_5$ is hydrogen or halogen; and $R_6$ is hydrogen or fluorine; can be used as antiinflammatory agents.

15 Claims, No Drawings

17-ALKYLTHIO (AND ARYLTHIO)-1',2',3',4'-TETRAHYDROANDROSTENO [16 α, 17 α-B]NAPHTHALENES AND DERIVATIVES

SUMMARY OF THE INVENTION

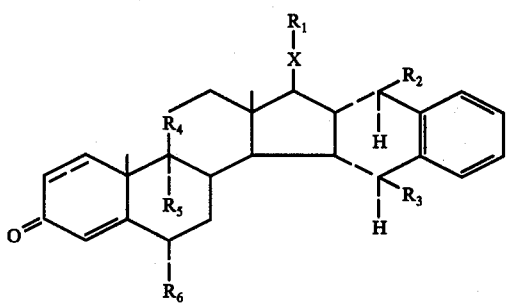

can be used as antiinflammatory agents. In formula I, and throughout the specification, the symbols are as defined below.

X is

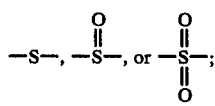

$R_1$ is alkyl, aryl or acyloxyalkyl;
$R_2$ and $R_3$ are the same or different and are hydrogen, alkyl, alkoxy, carboalkoxy, formyl,

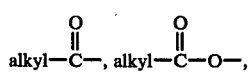

hydroxy, halogen, phenyl or cyano, with the proviso that when $R_2$ and $R_3$ are different, one of $R_2$ and $R_3$ is hydrogen;
$R_4$ is carbonyl, β-hydroxymethylene or β-acyloxymethylene;
$R_5$ is hydrogen or halogen; and
$R_6$ is hydrogen or fluorine.

A dotted line in the 1,2 position of a structural formula in this disclosure indicates the optional presence of ethylenic unsaturation.

The term "aryl", as used throughout the specification, refers to phenyl or phenyl substituted with one or two alkyl, alkoxy or halogen substituents.

The term "halogen", as used throughout the specification, refers to fluorine, chlorine, bromine and iodine.

The terms "alkyl" and "alkoxy", are used throughout the specification, refer to groups having 1 to 10 carbon atoms.

The term "acyloxy", as used throughout the specification, whether by itself or as part of a larger group, refers to a group having the formula

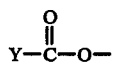

wherein Y is alkyl or aryl.

DETAILED DESCRIPTION OF THE INVENTION

The steroids of this invention can be prepared utilizing as starting materials androstenes having the formula

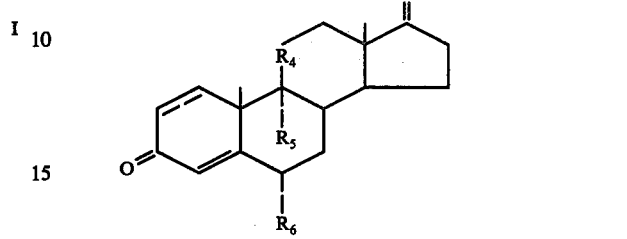

Reaction of an androstene of formula II with a thiol compound having the formula

in the presence of a Lewis acid (e.g., boron trifluoride etherate), yields an intermediate having the formula

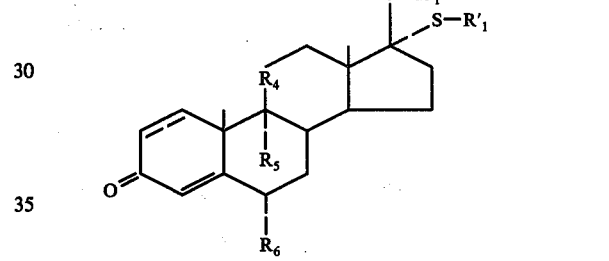

In formulas III and IV, and throughout the specification, $R'_1$ is alkyl or aryl. The reaction can be run in an organic solvent (e.g., a halogenated hydrocarbon), or a mixture of organic solvents. The use of some glacial acetic acid improves yields. Reaction conditions are not critical, and the reaction can be conveniently run at room temperature, preferably in an inert atmosphere (e.g., argon or nitrogen). Better yields may be obtained with relatively short reaction times (less than 1 hour).

An androstene of formula IV can be converted to the corresponding steroid having the formula

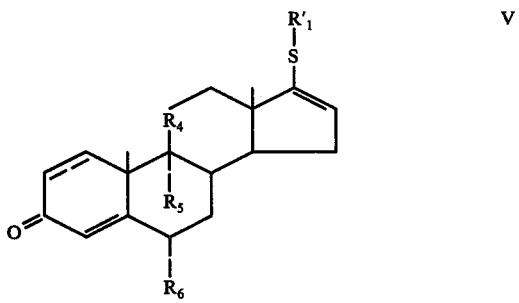

by simply heating the steroid in an inert solvent (e.g., diethylbenzene or dichlorobenzene).

The steroid products of formula I wherein $R_1$ is alkyl or aryl and X is divalent sulfur can be obtained by reacting a steroid of formula V with a benzocyclobutene having the formula

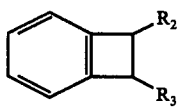 VI

The reaction can be run with, or without, an inert solvent. Preferably the reaction will be run neat, in an inert atmosphere, at temperatures up to the boiling point of the reaction mixture. The product of the above reaction has the formula

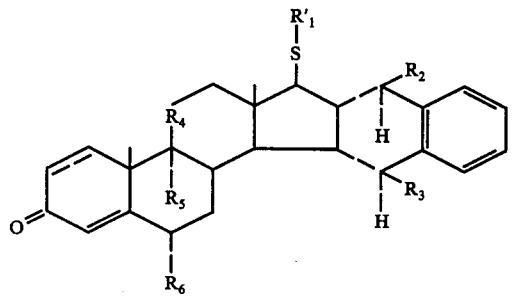 VII

Oxidation of an androstene of formula VII with a peracid (e.g., m-chloroperbenzoic acid), a peracid salt (e.g., sodium m-periodate) or a peroxide (e.g., hydrogen peroxide) yields the corresponding sulfinyl product having the formula

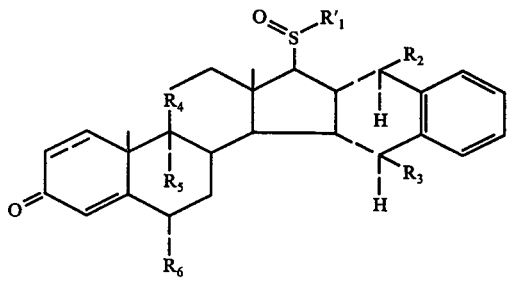 VIII or the corresponding sulfonyl product having the formula

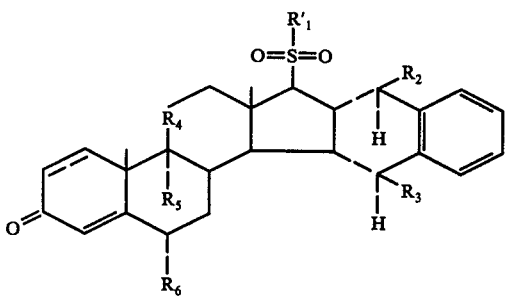 IX

The use of one equivalent of oxidizing agent will yield predominantly the sulfinyl derivative of formula VIII and the use of two or more equivalents of oxidizing agent will yield predominantly the sulfonyl derivative of formula IX. Metachloroperbenzoic acid is the preferred oxidizing agent. The oxidation reaction can be run in an organic solvent, e.g., a halogenated hydrocarbon such as chloroform.

Those steroids of formula I wherein $R_1$ is acyloxyalkyl can be prepared by first oxidizing a steroid of formula V, wherein $R'_1$ is alkyl, using one equivalent of oxidizing agent, to obtain a steroid having the formula

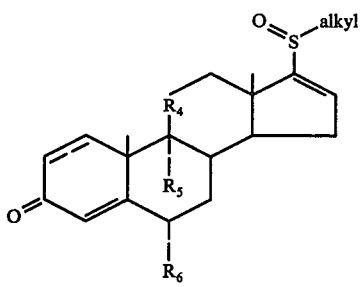 X

A 17-alkylsulfinyl steroid of formula X can be reacted with an appropriate acid anhydride, and a basic catalyst such as the sodium salt of the corresponding acid, to yield the corresponding 17-[[(acyloxy)alkyl]thio]steroid having the formula

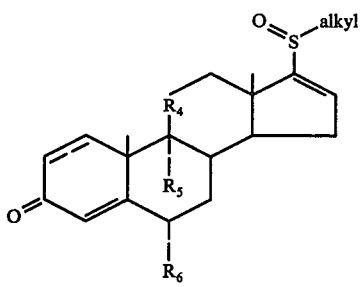 XI

Reaction of a steroid of formula XI with a benzocyclobutene of formula VI yields a product of formula I wherein $R_1$ is acyloxyalkyl and X is divalent sulfur. These steroids can be oxidized as described above to yield the corresponding steroids of formula I wherein X is $$-\overset{O}{\underset{}{\overset{\|}{S}}}-\ \text{or}\ -\overset{O}{\underset{\underset{O}{\|}}{\overset{\|}{S}}}-.$$

The 11β-acyloxy derivatives of formula I can be obtained by acylating the corresponding 11β-hydroxy steroid of formula I, by acylating the corresponding 11β-hydroxy steroid of formula II and proceeding as described above, or by acylating a corresponding 11β-hydroxy steroid intermediate and proceeding as described above.

Additional processes for preparing the steroids of formula I are available. For example, the steroids of formula I wherein X is $$-\overset{O}{\underset{\underset{O}{\|}}{\overset{\|}{S}}}-$$

can be prepared by first oxidizing a steroid of formula V with two or more equivalents of oxidizing agent and subsequently reacting the resultant 17-sulfonyl-Δ$^{16}$-steroid with a benzocyclobutene of formula VI.

The oxidation of a 17-thio product to yield a 17-sulfinyl steroid of formula I results in a mixture of two isomers, which may be separated using conventional techniques.

The steroids of formula I can be used in lieu of known glucocorticoids in the treatment of inflammatory conditions; e.g., rheumatoid arthritis. They can be administered in the same manner as hydrocortisone, the dosage being adjusted for the relative potency of the particular steroid. Additionally, the steroids of this invention can be used topically in lieu of known glucocorticoids in the treatment of skin conditions such as dermatitis, psoriasis, sunburn, neurodermatitis, eczema or anogenital pruritus.

When given orally, the steroids of this invention may be used in a dosage range of 0.1 to 200 milligrams, preferably 0.3 to 100 milligrams, for a 70 kg. mammal. If administered topically, the steroids of this invention may be used in the range of 0.01 to 5.0% by weight, preferably 0.05 to 2.0% by weight, in a conventional cream, ointment, lotion or the like.

The following examples are specific embodiments of this invention.

EXAMPLE 1

9-Fluoro-1',2',3',4'-tetrahydro-11β-hydroxy-17-(methylthio)-androsta-1,4-dieno[16α,17α-b]naphthalene-3-one

(A)

9-Fluoro-11β-hydroxy-17,17-bis(methylthio)androsta-1,4-dien-3-one

A solution of 9-fluoro-11β-hydroxyandrosta-1,4-diene-3,17-dione (2.0 g) in glacial acetic acid (25 ml) is mixed at room temperature with a solution of methanethiol (2.4 g) in dichloromethane (16 ml) and boron trifluoride etherate (0.5 ml). After 1.5 hours, the mixture is poured into water and diluted with chloroform. The organic layer is then separated, washed with a dilute sodium bicarbonate solution and water, dried and evaporated in vacuo. The residue is absorbed on a column of silica gel (50 g). Elution of the column with chloroform removed the nonsteroidal impurities and a product resulting from thiol addition to $\Delta^1$. Subsequent elution with chloroform affords the desired material as a solid (957 mg). Finally, elution with chloroform-ethyl acetate (95:5) affords the unreacted steroid (345 mg). A specimen of the 957 mg solid is crystallized once from chloroform-methanol to afford the analytical sample of the title compound, melting point 305° C (dec.).

Anal. Calc'd. for $C_{21}H_{29}FO_2S_2$: C, 63.60, H, 7.37; F, 4.79; S, 16.17. Found: C, 63.48; H, 7.21; F, 4.95; S, 16.21.

(B)

9-Fluoro-11β-hydroxy-17-(methylthio)androsta-1,4,16-trien-3-one

A suspension of 9-fluoro-11β-hydroxy-17,17-bis-(methylthio)androsta-1,4-diene-3-one (3.6 g) in diethylbenzene (250 ml) is slowly distilled from a bath at 220° C. In a few minutes, a clear solution results and the starting material disappears. On cooling in an ice bath, the solution deposits small needles of the analytical specimen of the title compound, (2.9 g), melting point 268° C (dec.). (discoloration starts at 263° C).

Anal. Calc'd. for $C_{20}H_{25}FO_2S$: C, 68.93; H, 7.23; F, 5.00; S, 9.20. Found: C, 68.68; H, 7.20; F, 4.92; S, 9.09.

(C)

9-Fluoro-1',2',3',4'-tetrahydro-11β-hydroxy-17-(methylthio)-androsta-1,4-dieno[16α,17α-b]naphthalene-3-one A suspension of 9-fluoro-11β-hydroxy-17-(methylthio)-androsta-1,4,16-trien-3-one (1.0 g) in benzocyclobutene (35 ml) is refluxed under an atmosphere of nitrogen. In 40 hours, a clear solution results. After 90 hours, distillation of the mixture affords unreacted benzocyclobutene (10 g). The residual oil is cooled, diluted with chloroform-hexane (1:1) and absorbed on a column of silica gel (60 g). Elution of the column with chloroform-hexane (1:1 to 7:3) removes decomposition products from benzocyclobutene. Further elutions with chloroform afford a mixture of the starting material and the title compound (1.05 g) and the homogeneous title compound (250 mg). The mixture of starting material and product is then rechromatographed over silica gel (50 g) to isolate another crop of the homogeneous title compound (276 mg). The 250 mg and 276 mg crops are combined and after one crystallization from chloroform-ethyl acetate afford 376 mg of the analytical specimen, melting point 265°–267° C (dec., discoloration starts at about 250° C).

Anal. Calc'd. for $C_{28}H_{33}FO_2S$: C, 74.30; H, 7.34; F, 4.20; S, 7.08. Found: C, 73.98; H, 7.29; F, 4.20; S, 6.76.

EXAMPLE 2

9-Fluoro-1',2',3',4'-tetrahydro-11β-hydroxy-17-(methylsulfonyl)-androsta-1,4-dieno[16α,17α-b]naphthalene-3-one

(A)

9-Fluoro-11β-hydroxy-17-(methylsulfonyl)androsta-1,4,16-triene-3-one

A solution of 9-fluoro-11β-hydroxy-17-(methylthio)-androsta-1,4,16-trien-3-one (1.0 g, see Example 1B) is dissolved by warming in a mixture of chloroform (130 ml) and absolute ethanol (20 ml). The solution is then cooled to room temperature and a solution of m-chloroperbenzoic acid (1.1 g of 90% peracid) is added. After 1.0 hour, the solution is washed with a dilute potassium carbonate solution and water, dried and evaporated to a solid. This is washed with hot ethyl acetate and filtered to afford the title compound as a colorless solid (1.06g), melting point 335°–337° C (dec.).

(B)

9-Fluoro-1',2',3',4'-tetrahydro-11β-hydroxy-17-(methylsulfonyl)androsta-1,4-dieno[16α,17α-b]naphthalene-3-one A solution of 9-fluoro-11β-hydroxy-17-(methylsulfonyl)androsta-1,4,16-triene-3-one (0.5 g) in dichlorobenzene (20.0 ml) and benzocyclobutene (4.0 ml) is heated in a bath a 170°–175° C under nitrogen for 40 hours. The solution is then cooled, poured on a column of silica gel (35 g) and the column eluted successively with chloroform-hexane (1:1), chloroform and chloroform-ethyl acetate (8:2 and 1:1) to afford from the chloroform-ethyl acetate eluates the title compound (585 mg), which had a trace of a less polar impurity as shown by thin-layer chromatography. Dissolution of this in ethyl acetate containing some methanol, evaporation of most of the methanol on a steam bath and cooling to ambient temperature affords 270 mg of the homogeneous analytical specimen of the title compound, melting point 254°–255° C (dec.; discoloration starting from 250° C).

Anal. Calc'd. for $C_{28}H_{33}FO_4S$: C, 69.39; H, 6.86; F, 3.92; S, 6.62. Found: C, 69.30; H, 6.73; F, 4.07; S, 6.60.

EXAMPLE 3

4′β-Ethoxy-9-fluoro-1′,2′,3′,4′-tetrahydro-11β-hydroxy-17-(methylsulfonyl)androsta-1,4-dieno[16α,17α-b]naphthalene-3-one A solution of 9-fluoro-11β-hydroxy-17(methylsulfonyl)-androsta-1,4,16-triene-3-one (400 mg, see Example 2A) in a mixture of dry toluene (125 ml) and dry o-dichlorobenzene (30 ml) containing 1-ethoxybenzocyclobutene (0.7 ml) is heated in a bath at 125° C for 3.0 hours. The solution is then cooled and absorbed on a dry column of silica gel (35 g). The column is eluted successively with chloroform-hexane (1:1), chloroform and chloroform-ethyl acetate (3:1) to afford from the eluates of the last two solvents the title compound (619 mg) contaminated with some impurities. Two crystallizations of this material from ethyl acetate-hexane afford needles of the homogeneous title compound (430 mg), melting point 258°–260° C (dec., discoloration starts from 250° C).

Anal. Calc'd. for $C_{30}H_{37}FO_5S$: C, 68.15; H, 7.06: F, 3.59; S, 6.06. Found: C, 67.89; H, 7.07; F, 3.83; S, 5.99.

EXAMPLE 4

17-[[(Acetyloxy)methyl]sulfonyl]-9-fluoro-1′,2′,3′,4′-tetrahydro-11β-hydroxyandrosta-1,4-dieno[16α,17α-b]naphthalene-3-one

(A)

9-Fluoro-11β-hydroxy-17-(methylsulfinyl)androsta-1,4,16-trien-3-one

To a stirred solution of 1.0 g of 9-fluoro-11β-hydroxy-17-(methylthio)androsta-1,4,16-trien-3-one (see Example 1B) in chloroform (500 ml) is added a solution of 85% m-chloroperbenzoic acid (552 mg) in chloroform (10 ml) in the course of 3.0 minutes. In less than 10 minutes, the peracid and the starting steroid disappear. The solution is then washed with a dilute potassium carbonate solution and water, dried, concentrated (to about 10 ml) and diluted with ethyl acetate resulting in the precipitation of small, light needles of the analytical specimen of the title compound, (1.0 g), melting point 268°–269° C (dec.). This is a mixture of the two sulfinyl isomers.

Anal. Calc'd. for $C_{20}H_{25}FO_3S$: C, 65.90; H, 6.90; F, 5.00; S, 8.80. Found: C, 65.76; H, 6.98; F, 4.92; S, 9.09.

(B)

17-[[(Acetyloxy)methyl]thio]-9-fluoro-11β-hydroxyandrosta-1,4,16-trien-3-one

A mixture of 1.5 g of 9-fluoro-11β-hydroxy-17-(methylsulfinyl)androsta-1,4,16-trien-3-one, 70 ml of acetic anhydride and 2 g of fused sodium acetate is heated at 110° C under nitrogen for 2 hours. The acetic anhydride is partially removed by distillation under vacuum and the resulting slurry is diluted with 1:1 chloroform-water. The organic layer is separated, washed with diluted sodium bicarbonate solution, water, dried over anhydrous sodium sulfate and evaporated in vacuo. The residue is dissolved in 4:1 chloroform-hexane and chromatographed on a 40 g-silica gel column. Elution with 1:4 hexane-chloroform gives 940 mg of slightly impure material. Two crystallizations from acetone-hexane give 350 mg of the title compound, melting point 193°–194° C.

Anal. Calc'd. for $C_{22}H_{27}FO_4S$: C, 65.00; H, 6.70; F, 4.67; S, 7.89. Found: C, 64.75; H, 6.73; F, 4.39; S, 8.15.

(C)

17-[[(Acetyloxy)methyl]sulfonyl]-9-fluoro-11β-hydroxyandrosta-1,4,16-triene-3-one To a solution of 17-[[(acetyloxy)methyl]thio]-9-fluoro-11β-hydroxyandrosta-1,4,16-triene-3-one (507.6 mg) in chloroform (25 ml) is added a solution of 85–90% m-chloroperbenzoic acid (508 mg) in chloroform at ambient temperature. Within a few minutes the starting material disappears. The solution is then washed with a dilute sodium bicarbonate solution and water, dried and evaporated to afford 550 mg of the title compound as a solid. This contains only traces of impurities by thin layer chromatography and is used directly for the next reaction. A specimen (50 mg) is crystallized from ethyl acetate-toluene to afford 38 mg of the title compound as heavy prisms, melting point 186°–187° C.

(D)

17-[[(Acetyloxy)methyl]sulfonyl]-9-fluoro-1′,2′,3′,4′-tetrahydro-11β-hydroxyandrosta-1,4-dieno[16α,17α-b]-naphthalene-3-one A solution of 17-[[(acetyloxy)methyl]sulfonyl]-9-fluoro-11β-hydroxyandrosta-1,4,16-triene-3,20-dione (350 mg) and benzocyclobutene (1.0 ml) in o-dichlorobenzene (4.0 ml) containing 4,4′-thiobis-6-t-butyl-m-cresol (10 mg) is heated in a bath at 170° C for 24 hours in an atmosphere of dry nitrogen. Another 1.0 ml of benzocyclobutene is then added and the reaction is continued for 5.0 hours. The mixture is cooled, poured on a column of silica gel (30 g) and the column eluted successively with chloroform-hexane (1:1), chloroform and chloroform-ethylacetate (8:2) to afford successively in these solvents a nonsteroidal oil, a steroidal material (80 mg) and a mixture of the starting material and the title compound (280 mg). The 280 mg crop is subjected to preparative thin layer chromatography (one 2.0×200×200 mm silica gel plate, 3 developments) with chloroform-methanol (97:3) to isolate the title compound (190 mg). One crystallization from ethyl acetate affords the homogeneous analytical specimen as small crystals (165 mg), melting point 246°–248° C (dec., discoloration starts from about 210° C) with consistent spectral data.

Anal. Calc'd. for $C_{30}H_{35}FO_6S$: C, 66.40; H, 6.50; F, 3.50; S, 5.91. Found: C, 66.21; H, 6.38; F, 3.45; S, 5.79.

EXAMPLE 5

17-[[(Acetyloxy)methyl]sulfonyl]-4′β-ethoxy-9-fluoro-1′,2′,3′,4′-tetrahydro-11β-hydroxyandrosta-1,4-dieno[-16α,17α-b]naphthalene-3-one A solution of 17-[[(Acetyloxy)methyl]sulfonyl]-9-fluoro-11β-hydroxyandrosta-1,4,16-triene-3-one (500 mg., see Example 4C) in toluene (15 ml) containing 1-ethoxybenzocyclobutene (0.5 g) is heated in a bath at 120°–130° C under nitrogen for 2.0 hours when the starting material disappears. The solution is then evaporated and the residue subjected to chromatography on a column of silica gel (20 g). Elution of the column with chloroform-hexane (1:1) affords first nonsteroidal impurities. (Further elution with this solvent mixture affords a solid (350 mg), which on the basis of spectral data and thin layer chromatography behavior is believed to be the 11-[ethoxy(2-methylphenyl)methyl]ether of the title compound). Further elution of the column with chloroform and chloroform-ethyl acetate (9:1) affords the title compound (358 mg). Two crystallizations from ethyl acetate afford the analytical specimen (228 mg), melting point 160°–210° C (dec., decomposes with gas evolution at 160° C and melts completely at 210° C).

Anal. Calc'd. for $C_{32}H_{39}FO_7S$: C, 65.51; H, 6.70; F, 3.00; S, 5.46. Found: C, 65.22; H, 6.63; F, 3.16; S, 5.35.

EXAMPLE 6

9-Fluoro-1',2',3',4'-tetrahydro-11β-hydroxy-17-(methylsulfinyl)-androsta-1,4-dieno[16α,17α-b]naphthalene-3-one (isomers A and B)

To a stirred solution of 9-fluoro-1',2',3',4'-tetrahydro-11β-hydroxy-17-(methylthio)androsta-1,4-dieno[16α,17α-b]-naphthalene-3-one (527 mg, see Example 1) in dichloromethane (30 ml) at room temperature is added dropwise a solution of 85% m-chloroperbenzoic acid (238 mg) in dichloromethane (15 ml). In less than 20 minutes the starting steroid and the peracid disappear as indicated respectively by thin-layer chromatography and a starch-potassium iodide paper test. The solution was then washed with a dilute potassium carbonate solution and water, dried, evaporated and was subjected to preparative layer chromatography to isolate compounds as solids. These are listed below in the order of increasing $R_f$ values.

| Compound | Weight |
|---|---|
| 1 | 246 mg |
| 2 | 209 mg |
| 3 | 40 mg |

Compound 1 (246 mg) is crystallized once from chloroform-ethyl acetate to afford the analytical specimen of the title compound (Isomer A), melting point 297°–298° C (dec.).

Anal. Calc'd. for $C_{28}H_{33}FO_3S$: C, 71.77; H, 7.10; F, 4.05; S, 6.84. Found: C, 71.99; H, 7.24; F, 4.31; S, 6.96.

Compound 2 (209 mg) is crystallized once from chloroform-ethyl acetate to afford the analytical specimen of Isomer B (180 mg), melting point 255°–256° C (dec.).

Anal. Calc'd. for $C_{28}H_{33}FO_3S$: C, 71.77; H, 7.10; F, 4.05; S, 6.84. Found: C, 71.54; H, 6.99; F, 4.15; S, 6.74.

EXAMPLES 7–17

Following the procedure of Example 1, but substituting the steroid listed in column I for 9-fluoro-11β-hydroxyandrosta-1,4-diene-3,17-dione, the compound listed in column II for methanethiol, and the compound listed in column III for benzocyclobutene, yields the steroid listed in column IV.

| | Column I | Column II | Column III | Column IV |
|---|---|---|---|---|
| 7) | 11β-hydroxyandrosta-1,4-diene-3,17-dione | thiophenol | trans-1,2-diethoxy-benzocyclobutene | 1'β,4'β-diethoxy-1',2',3',4'-tetrahydro-11β-hydroxy-17-(phenylthio)androsta-1,4-dieno-[16α,17α-b]naphthalene-3-one |
| 8) | 9-bromoandrosta-4-ene-3,11,17-trione | ethanethiol | 1-ethyl-1,2-2-dihydro-benzocyclobutene | 9-bromo-4'β-ethyl-17-(ethylthio)-1',2',3',4'-tetrahydroandrosta-4-eno[16α,17α-b]naphthalene-3,11-dione |
| 9) | 9-fluoro-11β-hydroxyandrosta-1,4-diene-3,17-dione | n-butanethiol | 1-carbomethoxybenzo-cyclobutene | 17-(butylthio)-9-fluoro-1',2',3',4'-tetrahydro-11β-hydroxy-3-oxoandrosta-1,4-dieno[16α,17α-b]naphthalene-4'β-oic acid, methyl ester |
| 10) | 11β-hydroxyandrosta-4-ene-3,17-dione | n-propanethiol | 1-formylbenzocyclo-butene | 4'β-formyl-1',2',3',4-tetrahydro-11β-hydroxy-17-(propylthio)androsta-4-eno[16α,17α-b]naphthalene-3-one |
| 11) | 9-chloro-11β-hydroxyandrosta-1,4-diene-3,17-dione | thiophenol | 1-acetyloxybenzocyclo-butene | 4'β-(acetyloxy)-9-chloro-1',2',3',4'-tetrahydro-11β-hydroxy-17-(phenylthio-androsta-1,4-dieno[16α,17α-b]naphthalene-3-one |
| 12) | 9-iodo-11β-hydroxyandrosta-1,4-diene-3,17-dione | 1-mercapto-2-methylbenzene | 1-acetylbenzocyclo-butene | 4'β-acetyl-1',2',3',4'-tetrahydro-11β-hydroxy-9-iodo-17-[(2-methylphenyl)thio]androsta-1,4-dieno-[16α,17α-b]naphthalene-3-one |
| 13) | 9-fluoro-11β-hydroxyandrosta-1,4-diene-3,17-dione | 1-mercapto-2-methoxybenzene | trans-1,2-dibromobenzo-cyclobutene | 1'β,4'β-dibromo-9-fluoro-1',2',3',4'-tetrahydro-β-hydroxy-17-[(2-methoxyphenyl)-thio]androsta-1,4-dieno-[16α,17α-b]naphthalene-3-one |
| 14) | 9-fluoro-11β-hydroxyandrosta-4-ene-3,17-dione | 1-chloro-4-mercaptobenzene | trans-1,2-dihydroxy-benzocyclobutene | 17-[(4-chlorophenyl)thio]-fluoro-1',2',3',4'-tetrahydro-1'β,4'β,11β-trihydroxyandrosta-4-eno[16°,17α-b]-naphthalene-3-one |
| 15) | 11β-hydroxyandrosta-1,4-diene-3,17-dione | methanethiol | 1-phenyl-1,2-dihydro-benzocyclobutene | 1',2',3',4'-tetrahydro-11β-hydroxy-17-(methylthio)-4'β-phenylandrosta-1,4-dieno-[16α,17α-b]naphthalene-3-one |
| 16) | 11β-hydroxyandrosta-1,4-diene-3,17-dione | methanethiol | 1-cyano-1,2-dihydro-benzocyclobutene | 1',2',3',4'-tetrahydro-11β-hydroxy-17-(methylthio)-3-oxoandrosta-1,4-dieno-[16α,17α-b]naphthalene-4'β-carbonitrile |
| 17) | 6°,9-difluoro-11β-hydroxy-androsta-4-ene-3,17-dione | 1-bromo-4-mercaptobenzene | trans-1,2-dihydroxy-benzocyclobutene | 17-[(4-bromophenyl)thio]-6α,9-difluoro-1',2',3',4'-tetrahydro-1'β,4'β,11β-trihydroxyandrosta-4-eno[16α,17α-b]naphthalene-3-one |

What is claimed is:
1. A steroid having the formula

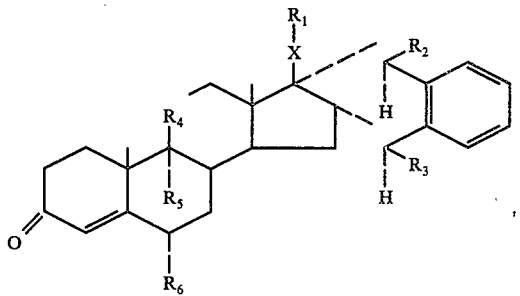

or the 1,2-dehydro derivative thereof, wherein X is

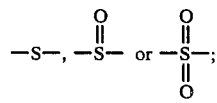

$R_1$ is alkyl, aryl or acyloxyalkyl; $R_2$ and $R_3$ are the same or different and are hydrogen, alkyl, alkoxy, carboalkoxy, formyl,

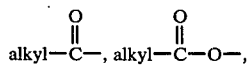

hydroxy, halogen, phenyl or cyano, with the proviso that when $R_2$ and $R_3$ are different, one of $R_2$ and $R_3$ is hydrogen; $R_4$ is carbonyl, β-hydroxymethylene or β-acyloxymethylene; $R_5$ is hydrogen or halogen; and $R_6$ is hydrogen or fluorine; wherein the term "aryl" refers to phenyl or phenyl substituted with one or two alkyl, alkoxy or halogen substituents; the term "acyloxy" refers to a group having the formula $$\overset{O}{\underset{\|}{Y-C-O-}}$$

wherein Y is alkyl or aryl; and the terms "alkyl" and "alkoxy" refer to groups having 1 to 10 carbon atoms.

2. A steroid in accordance with claim 1 wherein X is —S—.

3. A steroid in accordance with claim 1 wherein X is

4. A steroid in accordance with claim 1 wherein X is

5. A steroid in accordance with claim 1 wherein $R_1$ is alkyl.

6. A steroid in accordance with claim 1 wherein $R_1$ is aryl.

7. A steroid in accordance with claim 1 wherein $R_1$ is acyloxyalkyl.

8. A steroid in accordance with claim 1 wherein $R_2$ and $R_3$ are hydrogen.

9. A steroid in accordance with claim 1 wherein $R_4$ is β-hydroxymethylene, $R_5$ is fluorine, and $R_6$ is hydrogen.

10. The steroid in accordance with claim 1, 9-fluoro-1',2',3',4'-tetrahydro-11β-hydroxy-17-(methylthio)androsta-1,4-dieno[16α,17α-b]naphthalene-3-one.

11. The steroid in accordance with claim 1, 9-fluoro-1',2',3',4'-tetrahydro-11β-hydroxy-17-(methylsulfonyl)androsta-1,4-dieno[16α,17α-b]naphthalene-3-one.

12. The steroid in accordance with claim 1, 4'β-ethoxy-9-fluoro-1',2',3',4'-tetrahydro-11β-hydroxy-17-(methylsulfonyl)-androsta-1,4-dieno[16α,17α-b]naphthalene-3-one.

13. The steroid in accordance with claim 1, 17-[[(acetyloxy)methyl]sulfonyl]-9-fluoro-1',2',3',4'-tetrahydro-11β-hydroxyandrosta-1,4-dieno[16α,17α-b]naphthalene-3-one.

14. The steroid in accordance with claim 1, 17-[[(acetyloxy)methyl]sulfonyl]-4'β-ethoxy-9-fluoro-1',2',3',4'-tetrahydro-11β-hydroxyandrosta-1,4-dieno[16α,17α-b]naphthalene-3-one.

15. The steroid in accordance with claim 1, 9-fluoro-1',2',3',4'-tetrahydro-11β-hydroxy-17-(methylsulfinyl)-androsta-1,4-dieno[16α,17α-b]naphthalene-3-one.

* * * * *

UNITED STATES PATENT AND TRADEMARK OFFICE
CERTIFICATE OF CORRECTION

PATENT NO. : 4,091,036  
DATED : May 23, 1978  
INVENTOR(S) : Ravi K. Varma

Page 1 of 5

It is certified that error appears in the above-identified patent and that said Letters Patent are hereby corrected as shown below:

On the abstract page in the title "[16α,17α-B]" should read --[16α,17α-b]--

On the abstract page in the abstract the formula should read

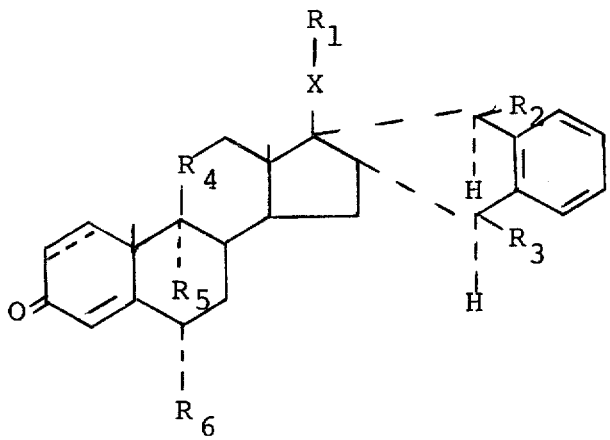

In column I, in the title "[16α,17α-B]" should read --[16α,17α-b]--

Column I, before the first structure insert --Steroids having the formula--

UNITED STATES PATENT AND TRADEMARK OFFICE
CERTIFICATE OF CORRECTION

PATENT NO. : 4,091,036
DATED : May 23, 1978
INVENTOR(S) : Ravi K. Varma

It is certified that error appears in the above-identified patent and that said Letters Patent are hereby corrected as shown below:

In column I, structural formula I should read

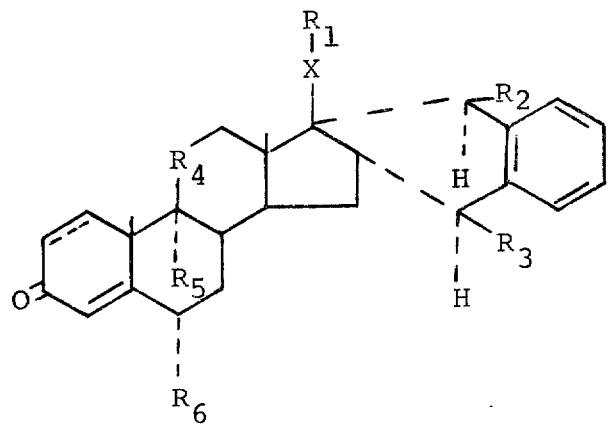

In column 3, structural formula VII should read

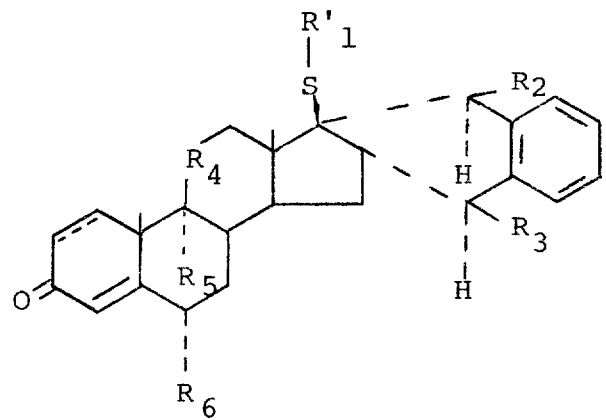

UNITED STATES PATENT AND TRADEMARK OFFICE
CERTIFICATE OF CORRECTION

PATENT NO. : 4,091,036
DATED : May 23, 1978
INVENTOR(S) : Ravi K. Varma

It is certified that error appears in the above-identified patent and that said Letters Patent are hereby corrected as shown below:

In column 3, structural formula VIII should read

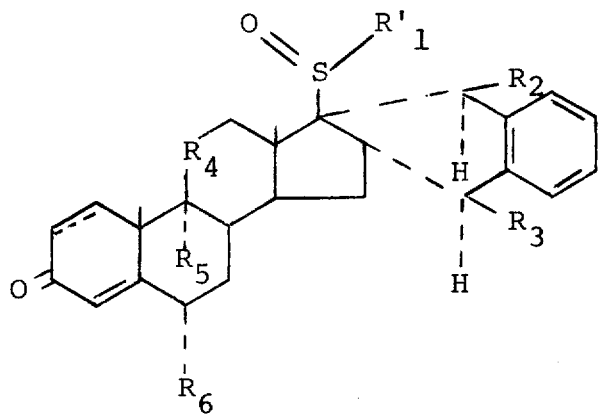

In column 3, structural formula IX should read

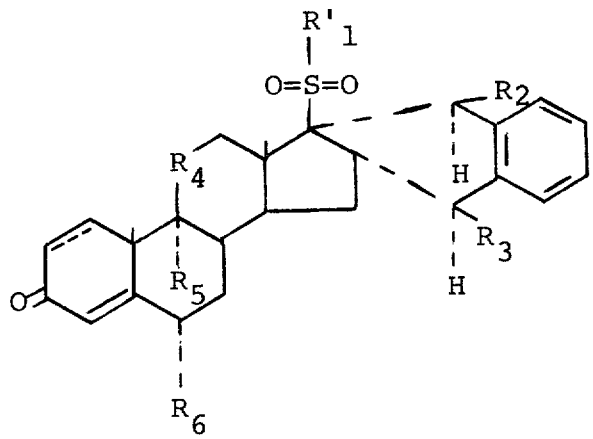

UNITED STATES PATENT AND TRADEMARK OFFICE
CERTIFICATE OF CORRECTION

PATENT NO. : 4,091,036
DATED : May 23, 1978
INVENTOR(S) : Ravi K. Varma

It is certified that error appears in the above-identified patent and that said Letters Patent are hereby corrected as shown below:

In columns 9 and 10, Example 13, column IV "-β-" should read -- -11β- --

In columns 9 and 10, Example 14, column IV "thio]-" should read --thio]-9- --

In columns 9 and 10, Example 14, column IV "[16$^{O}$,17α-b]-" should read --[16α,17α-b]- --

In columns 9 and 10, Example 17, column I "6$^{O}$" should read --6α--

UNITED STATES PATENT AND TRADEMARK OFFICE
CERTIFICATE OF CORRECTION

PATENT NO. : 4,091,036
DATED : May 23, 1978
INVENTOR(S) : Ravi K. Varma

It is certified that error appears in the above-identified patent and that said Letters Patent are hereby corrected as shown below:

In claim 1 the structure should read

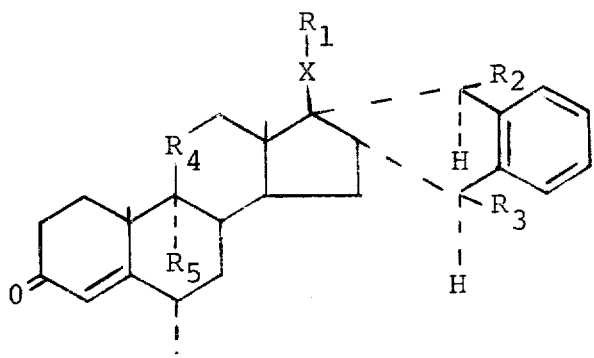

Signed and Sealed this

Fourteenth Day of November 1978

[SEAL]

Attest:

RUTH C. MASON
Attesting Officer

DONALD W. BANNER
Commissioner of Patents and Trademarks